United States Patent
Greenwald et al.

(10) Patent No.: US 8,706,244 B2
(45) Date of Patent: *Apr. 22, 2014

(54) FITTING OF BRIGHTNESS AS A FUNCTION OF CURRENT AMPLITUDE IN A VISUAL PROSTHESIS

(75) Inventors: Scott H. Greenwald, Seattle, WA (US); Matthew J. McMahon, Washington, DC (US); Ione Fine, Seattle, WA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 291 days.

This patent is subject to a terminal disclaimer.

(21) Appl. No.: 12/561,025

(22) Filed: Sep. 16, 2009

(65) Prior Publication Data

US 2010/0241192 A1     Sep. 23, 2010

Related U.S. Application Data

(60) Provisional application No. 61/097,475, filed on Sep. 16, 2008.

(51) Int. Cl.
*A61N 1/00* (2006.01)
*A61B 13/00* (2006.01)

(52) U.S. Cl.
USPC ............................................. 607/54; 600/558

(58) Field of Classification Search
USPC ..................... 607/53–54; 600/558
See application file for complete search history.

(56) References Cited

U.S. PATENT DOCUMENTS

| 5,109,844 | A |   | 5/1992  | de Juan, Jr. et al. |
| 5,935,155 | A |   | 8/1999  | Humayun et al. |
| 6,400,989 | B1 |  | 6/2002  | Eckmiller |
| 6,458,157 | B1 |  | 10/2002 | Suaning |
| 7,321,796 | B2 | * | 1/2008 | Fink et al. ................ 607/54 |
| 7,738,962 | B2 | * | 6/2010 | Greenberg et al. .......... 607/53 |
| 2006/0184062 | A1 | * | 8/2006 | Greenberg et al. ......... 600/558 |
| 2009/0005835 | A1 | * | 1/2009 | Greenberg et al. ......... 607/54 |

* cited by examiner

*Primary Examiner* — Christopher D Koharski
*Assistant Examiner* — Catherine Voorhees
(74) *Attorney, Agent, or Firm* — Scott B. Dunbar

(57) ABSTRACT

To accurately represent a visual scene a visual prosthesis must convey luminance information across a range of brightness levels. To do this, the brightness of phosphenes produced by an individual electrode should scale appropriately with luminance, and the same luminance should produce equivalently bright phosphenes across the entire electrode array. Given that the function relating current to brightness varies across electrodes, it is necessary to develop a fitting procedure that will permit brightness to be equated across an entire array. The current invention describes a method of performing a brightness fitting that normalizes brightness across electrodes. The method determines a set of parameters that are stored in the subjects Video Configuration File—the look-up table that converts the video camera input to stimulation profiles for each electrode. One electrode would be specified as the standard. Brightness rating would be carried out on that electrode so "rating" as a function of current amplitude was known for that electrode.

12 Claims, 16 Drawing Sheets

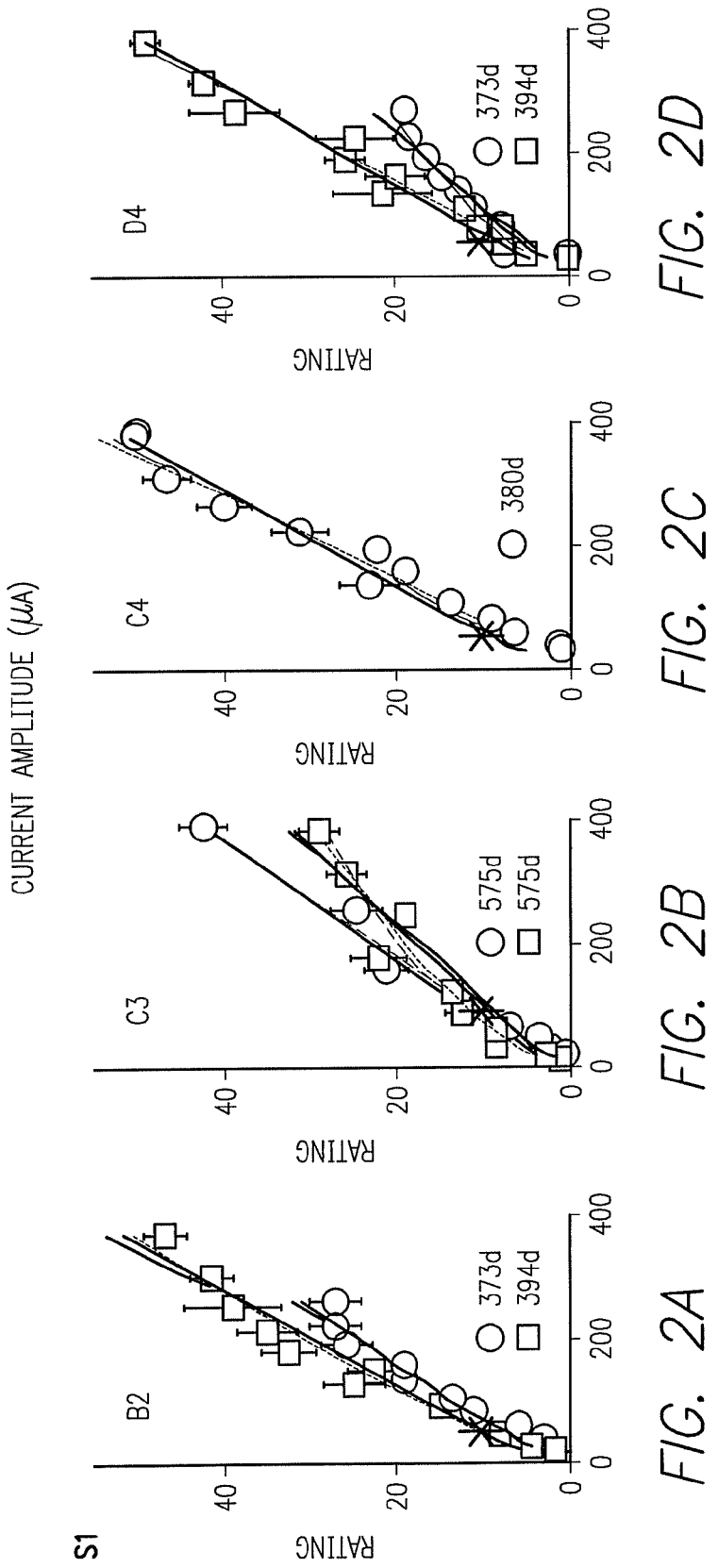

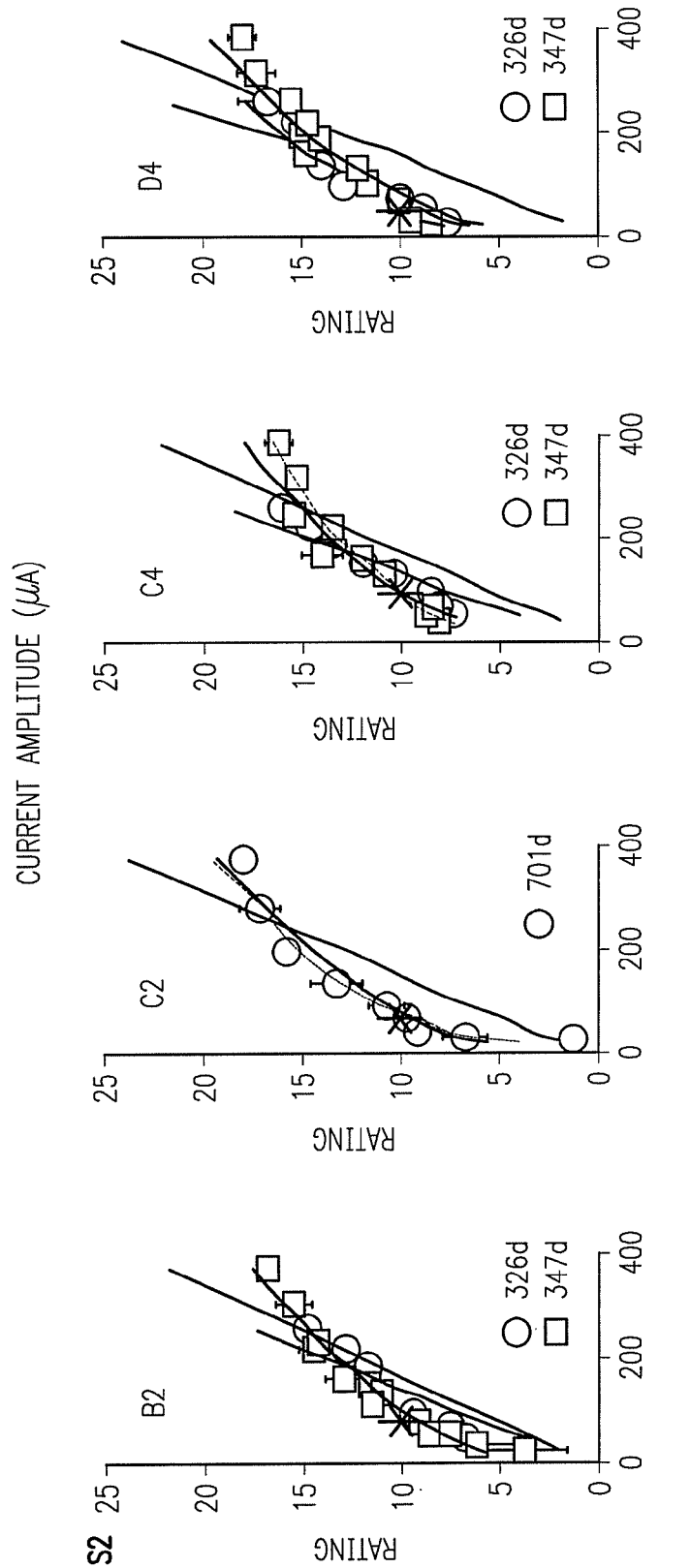

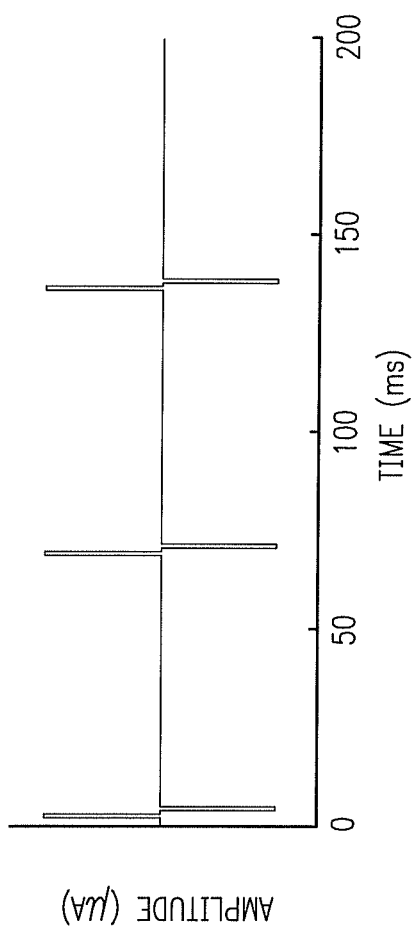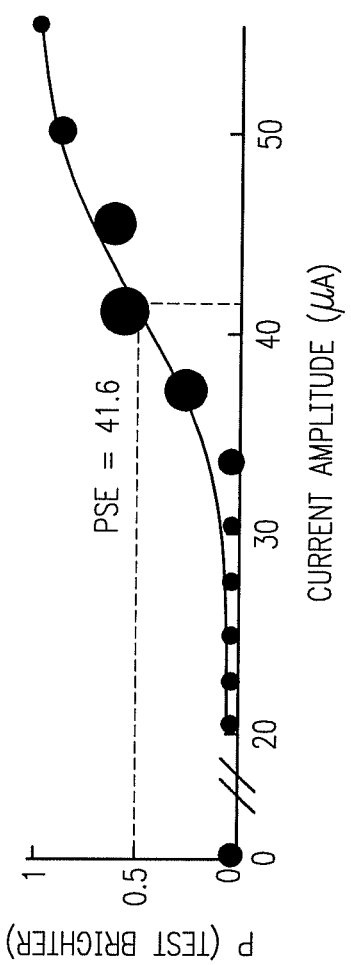
FIG. 3A
FIG. 3B

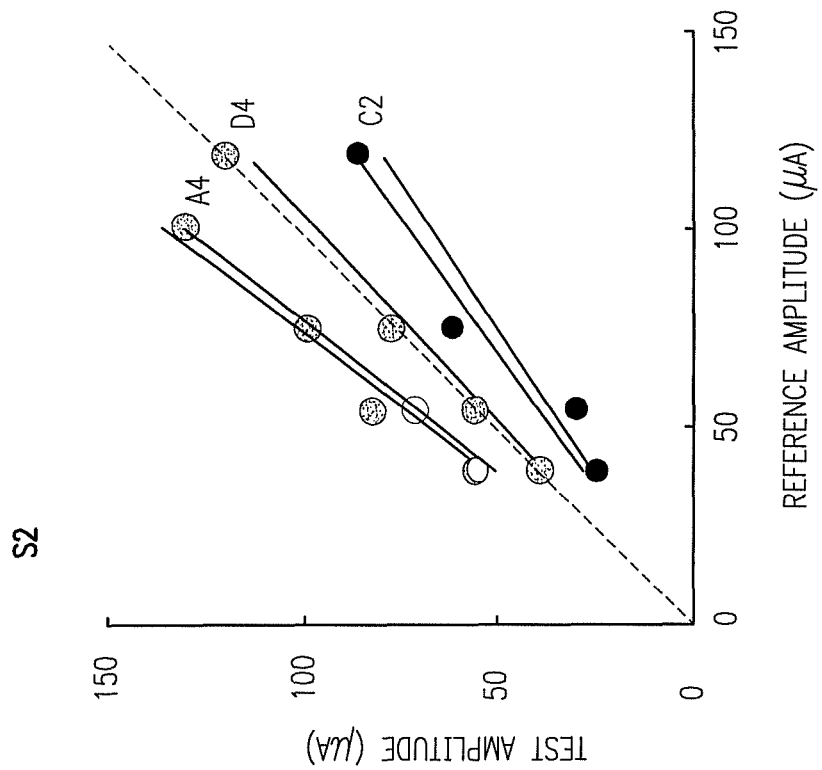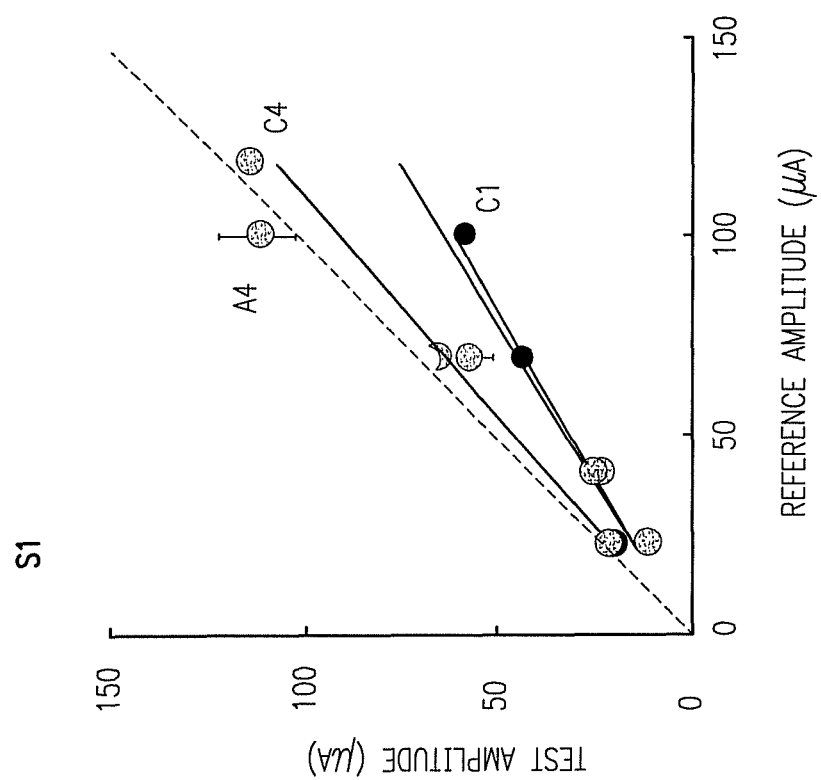
FIG. 4A
FIG. 4B

TABLE 1

| SUBJECT | ELECTRODE | POWER FIT W/ INTERCEPT | | | POWER FIT W/O INTERCEPT | | | LINEAR FIT | | | POWER FIT W/ FIXED B | |
|---|---|---|---|---|---|---|---|---|---|---|---|---|
| | | a | b | c | $R^2$ | a | b | c | $R^2$ | a | b | $R^2$ | a | $R^2$ |

| SUBJECT | ELECTRODE | a | b | c | $R^2$ | a | b | c | $R^2$ | a | b | $R^2$ | a | $R^2$ |
|---|---|---|---|---|---|---|---|---|---|---|---|---|---|---|
| S1 | D4 | 0.43 | 0.69 | 0.01 | 0.92 | 0.43 | 0.69 | 0.00 | 0.92 | 0.09 | 1.00 | 0.83 | 0.14 | 0.87 |
| S1 | D4 | 0.13 | 1.00 | 0.01 | 0.97 | 0.13 | 1.00 | 0.00 | 0.97 | 0.13 | 1.00 | 0.97 | 0.22 | 0.97 |
| S1 | B2 | 0.19 | 0.91 | 0.01 | 0.95 | 0.20 | 0.91 | 0.00 | 0.95 | 0.12 | 1.00 | 0.94 | 0.19 | 0.95 |
| S1 | B2 | 0.31 | 0.85 | 0.00 | 0.96 | 0.31 | 0.85 | 0.00 | 0.96 | 0.14 | 1.00 | 0.94 | 0.23 | 0.95 |
| S1 | C4 | 0.09 | 1.07 | 0.01 | 0.97 | 0.09 | 1.07 | 0.00 | 0.97 | 0.14 | 1.00 | 0.96 | 0.22 | 0.95 |
| S1 | C3 | 0.12 | 0.98 | 0.00 | 0.98 | 0.12 | 0.98 | 0.00 | 0.98 | 0.11 | 1.00 | 0.98 | 0.18 | 0.98 |
| S1 | C3 | 4.30 | 0.37 | −10.80 | 0.96 | 0.54 | 0.67 | 0.00 | 0.94 | 0.08 | 1.00 | 0.85 | 0.14 | 0.89 |
| AVERAGE | | 0.80 | 0.92 | 0.01 | 0.96 | 0.21 | 0.92 | 0.00 | 0.96 | 0.12 | 1.00 | 0.94 | 0.20 | 0.95 |
| S2 | D4 | 2.42 | 0.35 | −0.01 | 0.97 | 2.41 | 0.35 | 0.00 | 0.97 | 0.08 | 1.00 | −0.80 | 1.37 | 0.89 |
| S2 | D4 | 2.83 | 0.31 | 0.00 | 0.96 | 2.83 | 0.31 | 0.00 | 0.96 | 0.06 | 1.00 | −1.39 | 1.27 | 0.78 |
| S2 | B2 | 0.94 | 0.49 | 0.00 | 0.97 | 0.94 | 0.49 | 0.00 | 0.97 | 0.06 | 1.00 | 0.26 | 1.09 | 0.97 |
| S2 | B2 | 1.12 | 0.46 | 0.00 | 0.95 | 1.11 | 0.46 | 0.00 | 0.95 | 0.06 | 1.00 | 0.25 | 1.12 | 0.95 |
| S2 | C4 | 0.62 | 0.58 | 0.00 | 0.97 | 0.62 | 0.58 | 0.00 | 0.97 | 0.07 | 1.00 | 0.64 | 1.16 | 0.94 |
| S2 | C4 | 2.28 | 0.33 | 0.00 | 0.93 | 2.29 | 0.33 | 0.00 | 0.93 | 0.06 | 1.00 | −1.05 | 1.17 | 0.83 |
| S2 | C2 | 30.65 | 0.11 | −40.60 | 0.94 | 1.05 | 0.49 | 0.00 | 0.89 | 0.06 | 1.00 | 0.37 | 1.22 | 0.88 |
| AVERAGE | | 5.84 | 0.38 | −5.80 | 0.96 | 1.61 | 0.43 | 0.00 | 0.95 | 0.06 | 1.00 | −0.25 | 1.20 | 0.92 |

FIG. 6

TABLE 2

| SUBJECT | ELECTRODE | POWER FIT | | | LINEAR FIT | |
|---|---|---|---|---|---|---|
| | | a | b | $R^2$ | a | $R^2$ |
| S1 | B2 | 0.07 | 1.59 | 1.00 | 0.99 | 0.91 |
| S1 | B4 | 0.31 | 1.25 | 0.96 | 0.98 | 0.94 |
| S1 | A4 | 3.04 | 0.65 | 0.95 | 0.63 | 0.77 |
| S1 | C4 | 1.37 | 0.81 | 1.00 | 0.60 | 0.96 |
| S1 | C3 | 0.91 | 1.02 | 1.00 | 0.98 | 1.00 |
| S1 | C1 | 0.29 | 1.25 | 0.99 | 0.90 | 0.96 |
| *AVERAGE* | | *1.00* | *1.10* | *0.98* | *0.85* | *0.92* |
| S2 | B2 | 2.88 | 0.83 | 0.99 | 1.35 | 0.95 |
| S2 | B3 | 0.99 | 1.06 | 0.91 | 1.29 | 0.91 |
| S2 | A4 | 1.27 | 0.94 | 0.86 | 0.96 | 0.86 |
| S2 | D4 | 0.45 | 1.10 | 0.95 | 0.72 | 0.94 |
| S2 | D2 | 2.15 | 0.74 | 0.94 | 0.66 | 0.84 |
| S2 | C2 | 1.12 | 0.98 | 1.00 | 1.02 | 1.00 |
| *AVERAGE* | | *1.48* | *0.94* | *0.94* | *1.00* | *0.92* |

FIG. 7

FITTING OF BRIGHTNESS AS A FUNCTION OF CURRENT AMPLITUDE IN A VISUAL PROSTHESIS

CROSS REFERENCE TO RELATED APPLICATIONS

This application claims priority to U.S. Provisional Application 61/097,475, filed Sep. 16, 2008, for Brightness as a Function of Current Amplitude in Human Retinal Electrical Simulation. This application is related to and incorporates by reference U.S. patent application Ser. No. 11/357,680, filed Feb. 16, 2007, for Fitting of Brightness in a Visual Prosthesis, now issued as U.S. Pat. No. 7,738,692 on Jun. 15, 2010.

FIELD OF THE INVENTION

This application is related to visual prostheses and more particularly to method of mapping current to perceived brightness in fitting a visual prosthesis.

BACKGROUND

Retinitis pigmentosa and age-related macular degeneration are two of the more frequent causes of blindness in the developed world (Bunker et al., 1984; Heckenlively et al., 1988; Friedman et al., 2004). Both diseases are progressive and begin with the degeneration of photoreceptors. In later stages of these diseases, bipolar, amacrine, and ganglion cells are still present, though their numbers are significantly decreased (Santos et al., 1997; Humayun et al., 1999a; Jones et al., 2005) and their spatial organization and circuitry is significantly disorganized (Marc and Jones, 2003). There are over 180 different gene mutations that result in photoreceptor diseases for which there is currently no cure or treatment {Daiger, 2007 #4484}. Ideally, it would be possible to develop a treatment for these conditions that would not require targeting each genetic defect independently.

It has been shown that retinal electrical stimulation in human patients during acute clinical testing results in the perception of bright punctate phosphenes (Humayun et al., 1996). Indeed, there are several groups developing implantable microelectronic visual prostheses that produce percepts by electrically stimulating the remaining retinal neurons. The ultimate goal of these projects is to generate useful vision in blind patients by transforming a video stream into a spatial and temporal sequence of electrical pulses that represents meaningful visual information. To date, several groups have succeeded in generating visual percepts via electrical stimulation with implanted acute, semi-acute, and long-term retinal prostheses in human patients (Humayun et al., 1999b; Rizzo et al., 2003; Weiland et al., 2004; Yanai et al., 2007; Zrenner, 2007). However, creating a perceptually meaningful pattern of stimulation is dependent upon a detailed understanding of the perceived intensity of any given stimulation pattern, and to date the literature examining the perceptual consequences of electrical stimulation remains relatively sparse (Humayun et al., 1996; Weiland et al., 1999; Humayun et al., 2003; Rizzo et al., 2003; Mahadevappa et al., 2005; Yanai et al., 2007).

A successful visual prosthesis needs to produce regions of constant brightness across a range of brightness levels, and ideally these brightness levels should be consistent with the apparent brightness of objects as they appear to those with normal vision. Our goal was to examine how apparent brightness changes as a function of stimulation intensity.

As described in earlier work, thresholds (the current required to reliably detect whether stimulation has occurred) vary widely across subjects and across electrodes {Mahadevappa, 2005 #4213; {de Balthasar, 2008 #4485}. These differences in threshold are likely due to individual differences between subjects and across the retina of individual subjects. Potential factors that may affect sensitivity to electrical current include the degree of retinal degeneration and possibly subject age, differences in degeneration (Marc and Jones, 2003) or sensitivity to electrical current across each subject's retina, and differences in the distance of the array from the retina {de Balthasar, 2008}. These factors are also likely to be associated with differences in apparent brightness as a function of stimulation amplitude.

SUMMARY OF THE INVENTION

To accurately represent a visual scene a visual prosthesis must convey luminance information across a range of brightness levels. To do this, the brightness of phosphenes produced by an individual electrode should scale appropriately with luminance, and the same luminance should produce equivalently bright phosphenes across the entire electrode array. Given that the function relating current to brightness varies across electrodes, it is necessary to develop a fitting procedure that will permit brightness to be equated across an entire array.

The current invention describes a method of performing a brightness fitting that normalizes brightness across electrodes. The method determines a set of parameters that are stored in the subjects Video Configuration File—the look-up table that converts the video camera input to stimulation profiles for each electrode. One electrode would be specified as the standard. Brightness rating would be carried out on that electrode so "rating" as a function of current amplitude was known for that electrode.

An aspect of the invention is a method of fitting a visual prosthesis, comprising:
applying a plurality of stimuli via a first selected electrode to visual neural tissue; measuring brightness responses to said stimuli; deriving a first formula based upon said brightness responses; applying a stimuli via a second selected electrode measuring a brightness response to said stimuli; deriving a second formula based on said first formula and said brightness response to said second selected electrode; and generating said stimuli by applying said first formula and said second formula to visual input.

BRIEF DESCRIPTION OF THE DRAWINGS

FIGS. 2 a-h are graphs showing brightness versus current across multiple electrodes.

FIGS. 3 a-b show an example of a single data run where a test electrode is brightness matched to a reference electrode.

FIGS. 4a-b are graphs showing test amplitude versus reference amplitude demonstrating mapping brightness using linear scaling with one free parameter.

FIG. 6 is a table showing best fitting parameter values and percentage of variance.

FIG. 7 is a table showing best fitting parameter values and percentage of variance accounted for using two different models to describe brightness matching data.

DETAILED DESCRIPTION OF THE PREFERRED EMBODIMENT

To accurately represent a visual scene a visual prosthesis must convey luminance information across a range of brightness levels. To do this, the brightness of phosphenes produced by an individual electrode must scale appropriately with luminance, and the same luminance should produce equivalently bright phosphenes across the entire electrode array. The goal of the present invention is to examine how apparent brightness changes as a function of stimulation intensity, and to develop a system for mapping brightness across an array of electrodes to obtain consistent brightness responses.

Electrical stimulation of intact cells of the neural retina (amacrine, bipolar, and ganglion cells) using the visual prosthesis of the present invention reliably elicits visual percepts in human subjects blinded by retinitis pigmentosa. Here, we measure apparent brightness for a range of electrical amplitudes, using both subjective magnitude rating and brightness matching procedures in chronically implanted human subjects.

Figure 1:
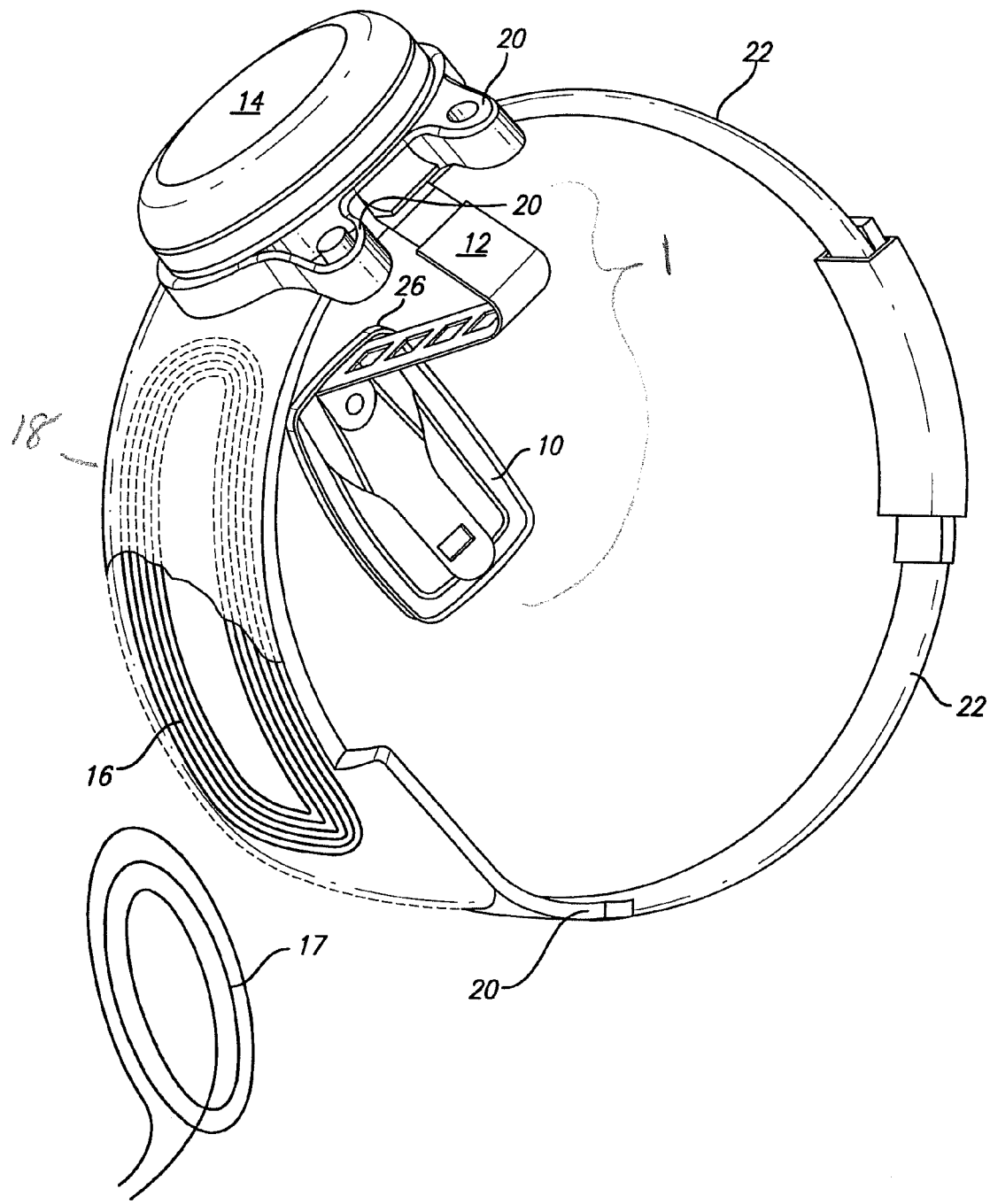
FIG. 1 is a perspective view of a the implanted portion of a visual prosthesis used in applying the present invention.

We found that apparent brightness can be described as a power function of stimulation intensity. The same model can also predict brightness matching across electrodes. These results suggest that a relatively simple model for scaling current across electrodes may, to a first approximation, be capable of producing equivalently bright phosphenes across an entire array. FIG. 1 shows a perspective view of the implanted portion of the preferred visual prosthesis. A flexible circuit 1 includes a flexible circuit electrode array 10 which is mounted by a retinal tack (not shown) or similar means to the epiretinal surface. The flexible circuit electrode array 10 is electrically coupled by a flexible circuit cable 12, which pierces the sclera and is electrically coupled to an electronics package 14, external to the sclera.

The electronics package 14 is electrically coupled to a secondary inductive coil 16. Preferably the secondary inductive coil 16 is made from wound wire. Alternatively, the secondary inductive coil 16 may be made from a flexible circuit polymer sandwich with wire traces deposited between layers of flexible circuit polymer. The secondary inductive coil receives power and data from a primary inductive coil 17, which is external to the body. The electronics package 14 and secondary inductive coil 16 are held together by the molded body 18. The molded body 18 holds the electronics package 14 and secondary inductive coil 16 end to end. The secondary inductive coil 16 is placed around the electronics package 14 in the molded body 18. The molded body 18 holds the secondary inductive coil 16 and electronics package 14 in the end to end orientation and minimizes the thickness or height above the sclera of the entire device. The molded body 18 may also include suture tabs 20. The molded body 18 narrows to form a strap 22 which surrounds the sclera and holds the molded body 18, secondary inductive coil 16, and electronics package 14 in place. The molded body 18, suture tabs 20 and strap 22 are preferably an integrated unit made of silicone elastomer. Silicone elastomer can be formed in a pre-curved shape to match the curvature of a typical sclera. However, silicone remains flexible enough to accommodate implantation and to adapt to variations in the curvature of an individual sclera. The secondary inductive coil 16 and molded body 18 are preferably oval shaped. A strap 22 can better support an oval shaped coil. It should be noted that the entire implant is attached to and supported by the sclera. An eye moves constantly. The eye moves to scan a scene and also has a jitter motion to improve acuity. Even though such motion is useless in the blind, it often continues long after a person has lost their sight. By placing the device under the rectus muscles with the electronics package in an area of fatty tissue between the rectus muscles, eye motion does not cause any flexing which might fatigue, and eventually damage, the device.

To accurately represent a visual scene a visual prosthesis must convey luminance information across a range of brightness levels. To do this, the brightness of phosphenes produced by an individual electrode should scale appropriately with luminance, and the same luminance should produce equivalently bright phosphenes across the entire electrode array. Given that the function relating current to brightness varies across electrodes, it is necessary to develop a fitting procedure that will permit brightness to be equated across an entire array.

The current invention describes a method of performing a brightness fitting that normalizes brightness across electrodes. The method determines a set of parameters that are stored in the subjects Video Configuration File—the look-up table that converts the video camera input to stimulation profiles for each electrode. One electrode would be specified as the standard. Brightness rating would be carried out on that electrode so "rating" as a function of current amplitude was known for that electrode.

As the numbers of electrodes in an array increase, it will be unfeasible to measure full brightness rating and/or brightness matching functions for each individual electrode. Here, we find that that brightness as a function of current amplitude can be described using a power function, with a single scaling factor as a free parameter as shown in FIG. 2.

Equivalently, it is possible to describe relative brightness across electrodes using a linear scaling with a single free parameter (the slope of the brightness matching function of FIG. 4). These results, show that it should be possible to normalize brightness across an entire array of electrodes by measuring a single parameter for each electrode. A single brightness matching measurement, if made at a relatively high amplitude, would be sufficient to describe relative sensitivity across electrodes, and thereby provide a simple method of creating the appearance of equally bright phosphenes across an entire array across a wide range of brightness levels.

So, suppose one wanted to create an image containing a bright square of brightness "15" inside a background of brightness "5". (These brightness values could be determined based on absolute luminance or by using any of the "back-pocket" models of lightness perception described in the vision literature on light perception.) As described above, one electrode would be chosen as a standard and brightness rating would be carried out on that electrode so "rating" as a function of current amplitude was known. The current amplitude values corresponding to "5" and "15" on the standard electrode would be sent to the video processing unit (VPU).

Suppose that a current value of 50 μAmps corresponded to a brightness rating of "5" and a current value of 150 μAmps corresponded to a brightness value of "15" for this standard electrode. The current required on each electrode can then be determined in the VPU by using the equation $c_n=k_n c_s$ (or equivalent lookup tables) where $c_s$ is the required current for any given electrode, $c_s$ is the desired current of the standard (50 or 150 µAmps in this example), and k has been previously determined using the brightness matching approach described above.

The result of this process will be a set of equibright electrodes where one set of electrodes are brightness matched to the brightness of the standard at 50 µAmps and the other set of electrodes are brightness matched to the brightness of the standard at 150 µAmps. This process can of course be carried out for any set of desired brightness levels.

One can also use an analogous process to create gradations of shading. Suppose one wanted a field shading gradually and linearly between a brightness of "5"-"15". One would find the current amplitude on the standard electrode corresponding to the desired intermediate brightness values, and then use the equation $c_n=k_n c_s$ to find the required current for any given electrode to produce that desired brightness level.

In Experiment 1, subjects rated the apparent brightness of pulse stimuli on individual electrodes, using a reference pulse of fixed amplitude. We found that apparent brightness as a function of current amplitude can be described using a simple power function.

In Experiment 2, a brightness matching technique was used to compare apparent brightness across pairs of electrodes. We found that the apparent brightness of a given electrode can be related to other electrodes on the array using the same simple power function model. These results suggest that a relatively simple model for scaling current across electrodes may, to a first approximation, be capable of producing equivalently bright phosphenes across an entire array.

Here we describe data from two subjects. The power and signal information can be independently controlled for each electrode. Stimulation consisted of a single pulse (Experiment 1) or pulse train (Experiment 2), consisting of biphasic, cathodic-first, charge-balanced square wave pulses. The durations of the individual cathodic and anodic phases were 0.975 ms, and each phase was separated by a 0.975 ms inter-pulse interval. Anodic and cathodic phases were always matched in amplitude.

Stimulation for test and reference pulses always consisted of a single biphasic, cathodic-first, charge-balanced square wave pulse, with a pulse duration of 0.975 and a 0.975 ms inter-pulse interval. For safety reasons, all pulse trains were charge-balanced using anodic pulses of equal width and amplitude. The reference pulse was fixed at a current amplitude chosen to be roughly 2.5 times the threshold amplitude for a single pulse on that electrode. Charge densities were always below 1 mC/cm$^2$.

Before beginning each testing session, subjects were repeatedly stimulated with the reference pulse and were told, "This reference pulse has brightness of 10 and we will present it to you before we begin each trial. Your task is to compare the brightness of the test pulse in each trial to the brightness of this reference pulse. If the test pulse seems to be twice as bright as the reference pulse then give it a rating of 20. If the test pulse seems to be half as bright as the reference pulse, then give it a rating of 5."

Once the subject reported feeling confident that they had a clear idea of the brightness of the reference pulse, we began the experiment. All subject ratings were provided verbally. On each trial, subjects were first presented with the reference pulse and were reminded that this pulse should be considered as having a brightness of 10. This reference pulse was quickly (~1 s) followed by the test pulse. Short auditory cues marked the onset of the presentation of both the reference and the test pulse. Subjects were then asked to verbally rate the apparent brightness of the test pulse, as compared to the reference pulse.

The test pulse was always presented on the same electrode as the reference pulse, and had a current amplitude that varied pseudo-randomly from trial to trial using the method of constant stimuli. The subjects were not told which test pulse current value had been presented on each trial, and no feedback was provided. Each test current amplitude was presented four times, and we calculated the mean and the standard error of brightness ratings for each stimulation amplitude across these four repetitions.

Patients typically reported that phosphenes appeared white or yellow in color, and round or oval in shape. At suprathreshold, percepts were reported as brighter and the shape occasionally became more complex than a simple round or oval shape. The shapes were reported as being approximately 0.5-2 inches in diameter at arm's length, corresponding to roughly 2-3 degrees of visual angle. In the case of S1 percepts seemed to increase (with a comparable scale factor) in size as well as brightness with increasing current amplitude. In the case of S2 percepts showed a small tendency to increase in size as well as brightness as a function of stimulation intensity, but increases in size were much smaller than brightness changes (data not shown). FIG. 2 shows brightness rating judgments for four electrodes for each of the two subjects. On each curve, the solid symbols represent mean subject ratings for each test electrode current amplitude and the star symbol represents the reference pulse (on the same electrode). Each data point represents four rating judgments. Where there are two data sets in a single subplot this represents repeated measurements on that electrode. Generally these repeated sessions were separated by 21 days. In one case, for subject S1, we repeated the same set of measurements on the same electrode twice in a single session.

In the case of S1 rating judgments seemed to vary significantly across repeated measurements, even when these two sets of measurements were carried out on the same day. Possible explanations for these inconsistencies include changes in her rating scale (both within and across sessions), adaptation effects within a single session, and movement of the electrode array across sessions. It should be noted that despite these differences across sessions, S1 did reliably report the standard as having a brightness of "10", and reliably (and with relatively small standard errors) reported increasing brightness with increasing current intensity, suggesting that she did understand the task. In the case of S2, he showed remarkable test-retest reliability even across separate sessions.

The curves through the data represent four models fits in descending order of complexity. The black dotted lines represent the best fitting power function with a multiplicative scalar and additive intercept ($B=aC^b+d$), where B is the brightness rating made by the subject, and C is the current amplitude of the test electrode. The black dashed lines represent the best fitting power function ($B=aC^b$) for each electrode with the assumption of an intercept of zero—i.e. that the subject would report a brightness of 0 when there was no stimulation, and equally that the subjects did not have a hard threshold, whereby very low current amplitude values led to a brightness rating of zero. The gray solid lines represent the best fitting linear function ($B=aC$), where again we assumed a zero intercept. The black solid lines once again represents the best fitting power function, without intercept ($B=aC^b$), however in this model b was fixed to be the median of the best-fitting values of b across all four electrodes for that subject. The parameter values a, b and d were determined using a standard least squared errors minimization technique.

It can be seen that these fits were very similar, in many cases the separate curves are overlapping. Best fitting parameter values and percentage of variance accounted for are shown in Table 1, FIG. 6.

FIG. 2 shows brightness rating judgments for two subjects. Four electrodes are shown for each subject, each column represents a different electrode. The x-axis represents the current amplitude of the test pulse. Solid symbols represent the mean brightness rating for that test amplitude. The star represents the current amplitude of the reference pulse, which was defined as having an apparent brightness of "10". Black dotted lines show power fit with three free parameters, black dashed lines show power fit with two free parameters, gray solid lines show linear fit with two free parameters, black solid lines show power fit with one free parameter. Single standard errors are shown.

Table 1, FIG. 6 shows the best fitting parameter values and percentage of variance accounted for using four different models to describe brightness rating data. For subject S1 there was little difference in the percentage of variance accounted for ($R^2$) between any of the models. For subject S2 the fits for the power functions accounted for significantly more variance than the linear fit, but there was little difference in the percentage of variance accounted for between any of the power functions.

These data could probably also be fit well using other nonlinear functions. One advantage of modeling our data using a power function with zero is that the exponent b (that describes the shape of the curve relating apparent brightness to current amplitude) is independent of the scaling parameter a. As described above, the amplitude of the reference pulse was chosen relatively arbitrarily to be approximately 2.5 times threshold. The independence of a and b allows the scaling factor a to compensate for the fact that the amplitude of our reference pulse was chosen relatively arbitrarily, leaving the parameter b to describe the nonlinearity in the amplitude-brightness function. If we had, for example, chosen the reference pulse to represent an apparent brightness of "5" rather than "10" then subjects' ratings of the brightness of the test pulses (which were rated relative to the reference pulse) would have been halved. This would result in a being halved, but b would remain unchanged. We found that for S1 b varied between 0.69 and 1.07 with a mean value of 0.92, and a median value of 0.91. For S2 b varied between 0.31 and 0.58 with a mean value of 0.43 and a median value of 0.46.

A second advantage of using a power fit is that magnitude data are traditionally fit using power functions. Rating data for electrical stimulation of cortex and the sensation of electrical stimulation of the skin are both better described with exponents greater than 1, implying an accelerating response at high stimulation amplitudes. However rating data for most sensory stimuli (including our data) are best fit with exponents less than 1, implying response saturation at high intensities. Indeed brightness rating data for a light point source presented in darkness has an exponent of 0.5. This exponent decreases as a function of the size of the light source: a 5 degree light stimulus has an exponent of 0.333. The difference in exponent between our two subjects corresponds to differences in the apparent size of their elicited percepts.

In summary, we find that brightness ratings can be well fit by a power function with zero intercept. Nonlinearities in the amplitude-brightness function did vary across our two subjects, but within each subject good fits could be obtained using a fixed value of b across all electrodes.

Experiment 2—Brightness Matching While brightness ratings have the advantage of providing an insight into the apparent brightness of the percept, these ratings are somewhat subjective. As shown in Experiment 1, we see significant variance in rating judgments even within a single session in a single subject. As a result, brightness ratings are also likely to vary substantially across sessions and across subjects.

In Experiment 2 we used a brightness matching technique, where subjects were asked to report which of two phosphenes appeared brighter. As well as comparing brightness matching performance within a single electrode, we also compared brightness across pairs of electrodes.

Both reference and test stimuli consisted of 200 ms, 15 Hz pulse trains that contained biphasic, cathodic-first, charge-balanced square wave pulses. The durations of the individual cathodic and anodic phases were 0.975 ms, and each phase was separated by a 0.975 ms inter-pulse interval. We used a smaller range of current amplitudes in the brightness matching experiment in order to remain below conservative long-term charge density limits of 0.35 $mC/cm^2$. One motivation for this is that in Experiment 2 we were using pulse trains rather than single pulses.

For each subject, the same reference electrode was used throughout the experiment. The reference electrode for S1 was C3 and the reference electrode for S2 was C2. The brightness of the reference electrode was compared to that of 6 test electrodes for each subject.

The choice of the reference electrode was based on two criteria: (1) the electrode threshold was chosen to be close to the median threshold value across all 16 electrodes, and (2) the electrode was chosen to be within an inner square of the array.

Subjects made brightness judgments between a pulse train presented on the reference electrode and a pulse train presented on the test electrode using a 2-interval forced choice procedure, where the subject reported which of two intervals appeared brighter on each trial. The presentation order for the reference and test electrode pulses was randomized for each trial, and there was a 900 ms delay between intervals.

Within each run (100 trials), the current amplitude of the reference pulse train was held constant, and the current amplitude of the test pulse train was adjusted using a 1 up-1 down staircase procedure based on which stimulus the subject had reported as being brighter in the previous trial. To make comparisons across a range of brightness levels, runs were carried out with the reference pulse train taking 5 different brightness levels spanning 23.3 µA to 119.7 µA. For each current value on the reference electrode, as the current amplitude of the test pulse train increases, so does the probability of the subject reporting that the test pulse train was brighter. We used a Monte Carlo simulation procedure to find the best fitting cumulative normal function to find the error value of the estimated point of subjective equality (PSE, the amplitude of the test pulse train for which the test and reference appear equally bright)

FIG. 3 shows an example of a single data run where the test electrode B4 was brightness matched to the reference electrode C3 (41.7 µA, 15 Hz pulse train). The x-axis represents the current amplitude of the test pulse train and the y-axis represents the probability that the subjects reported that the test pulse train was brighter than the reference pulse train. We used a Monte Carlo simulation procedure to find the best fitting cumulative normal function, which was used to calculate the estimated point of subjective equality. The data run shown here contained 100 trials; the size of each data point represents the number of trials at that test pulse train amplitude.

FIG. 3 shows example data showing how points of subjective equality (PSE, dashed lines) were calculated. The PSE is defined as the current amplitude on the test electrode where subjects report that the test electrode is brighter on 50% of trials. The size of each marker is proportional to the number of trials collected for that test current amplitude. Data shown here are for S1, in the condition where the reference electrode was compared to another electrode. The reference pulse was fixed at 41.09 µAmps.

FIG. 4 shows brightness matching between the reference and test electrodes for both subjects. Each point represents the amplitude on the test electrode required to reach the PSE for a fixed current amplitude on the reference electrode. The x-axis represents the current amplitude of the reference electrode and the y-axis represents the current amplitude of the test electrode.

FIGS. 4a and b plot brightness matching data for both subjects. For each subject we measured PSEs with the pulse amplitude on the reference electrode fixed at 5 different amplitude levels. The x-axis represents the amplitude of the pulse on the reference electrode. The y-axis represents the PSE on each of six test electrodes and the reference electrode brightness matched to itself. 520 µm electrodes are represented by large symbols, 260 µm electrodes by small symbols.

As would be expected, when the reference electrode was brightness matched to itself the curve of subjective equal brightness fell along a line of slope=1. In Experiment 1 we found that brightness as a function of current could be described using a power function ($B=aC^b$) The current on the test electrode ($C_T$) needed to match the brightness of the reference electrode at a given current amplitude ($C_R$) can therefore be described as $C_T=a_T/a_R C_R^{(b_R/b_T)}$. The black dotted lines show a fit to our brightness matching data using the model $C_T=aC_R^b$, where both a and b were allowed to vary. a represents $a_T/a_R$, and b represents $b_R/b_T$. The black solid lines represent a fit based on the model $C_T=aC_R$. The assumption that b=1 is of course equivalent to $b_R=b_T$, i.e. that the same power function can be applied across any electrode for a given subject.

Table 2 shows best fitting parameter values and percentage of variance accounted for using two different models to describe brightness matching data. Best fitting parameter values and percentage of variance accounted for with these two different fits are shown in Table 2. The model where b=1 again accounted for a large amount of the variance, suggesting that reasonable brightness matching can be carried out across electrodes by measuring a single parameter, a.

The value of a, has of course, a simple intuitive interpretation. A slope of 0.9 means that, for any current amplitude on the reference electrode, the test electrode only required 90% as much current as the reference electrode to appear equally bright. We found that slopes varied between 0.65-1.08 for S1, and between 0.94-1.41 for S2. I.e. the least sensitive electrode required 66% more current than the most sensitive electrode to create an appearance of equal brightness for S1 and required 50% more current for S2. We found that the slopes of these brightness matching functions was significantly shallower for large (520 µm) as compared to small (260 µm) electrodes. A 2 factor (subject x electrode size) ANOVA on brightness matching slopes found a significant effect of both subject (p=0.02) and electrode size (p=0.014), with no significant interaction between factors. In an earlier paper {de Balthasar, 2008}, we reported that thresholds were the same for 260 and 520 µm electrodes—however, as can be seen in FIG. 4, differences in sensitivity across different sizes of electrode at near threshold levels of stimulation were much smaller than at high current levels. This may also explain why we did not find a significant (p>0.05) correlation of slope with threshold.

Figure 5A:
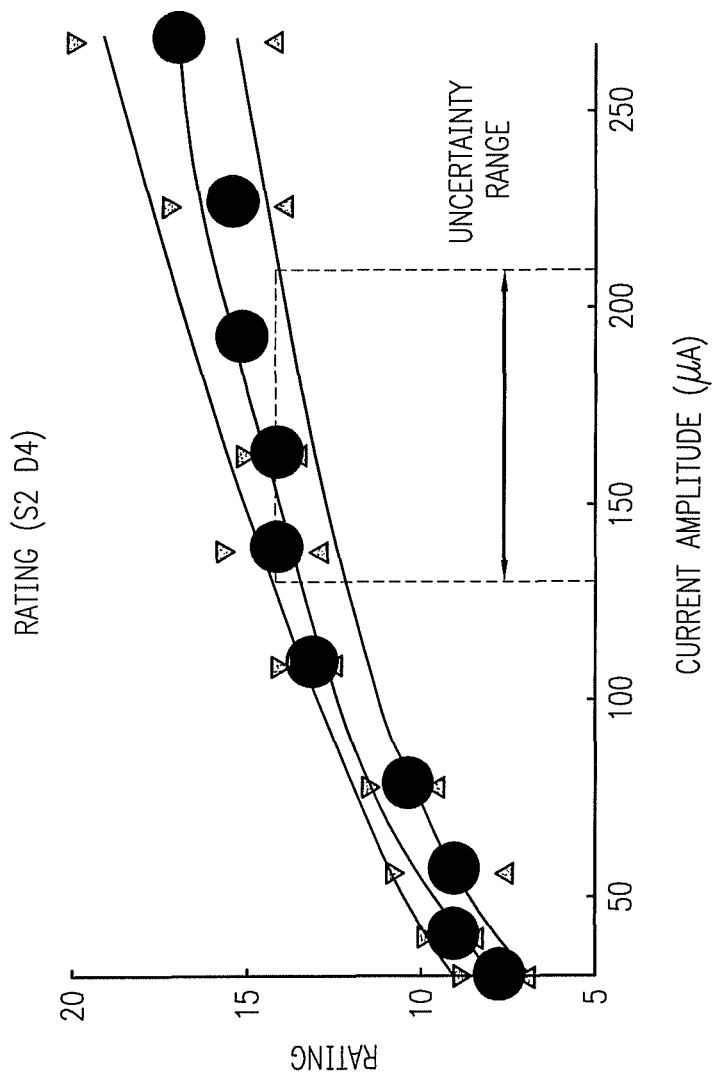
FIGS. 5a-c are graphs showing brightness rating versus brightness matching.

Comparison of measurement variability between brightness rating and matching measurements. The black solid line in FIG. 5a shows a single brightness rating function (re-plotted from FIG. 2) for electrode S2 D4, with gray triangles and lines representing +/−1 standard deviation in the brightness ratings. To compare variability in brightness rating judgments to brightness matching judgments it is necessary to convert variability in rating scores to variability in current amplitude. To do this we interpolated to find the points along the curves representing +/− one standard deviation along the y-axis, and found the corresponding amplitude values along the x-axis. If subjects were exquisitely accurate in assigning brightness ratings to changes in amplitude then we would expect this uncertainty range to be very small. If subjects show large amounts variability in assigning brightness ratings, then this uncertainty range would be large.

Figure 5B:
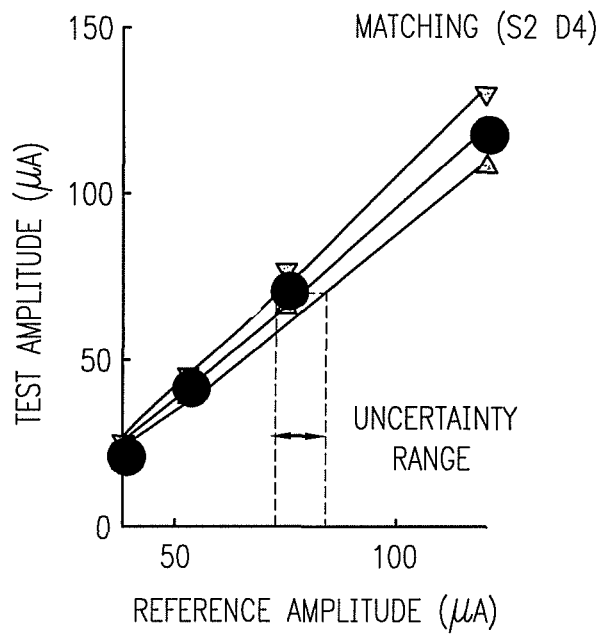

The black solid line in FIG. 5b shows a single brightness matching function (re-plotted from FIG. 4) for the same electrode. Once again, gray triangles and lines represent +/−1 standard deviation in the brightness match. We once again interpolated to find the uncertainty range for the test electrode. Again, if subjects were exquisitely sensitive to changes in amplitude then we would expect the current range over which subjects are uncertain whether the test of the reference pulse is brighter to be very small. If subjects are insensitive to changes in brightness then this uncertainty range would be large.

Figure 5C:
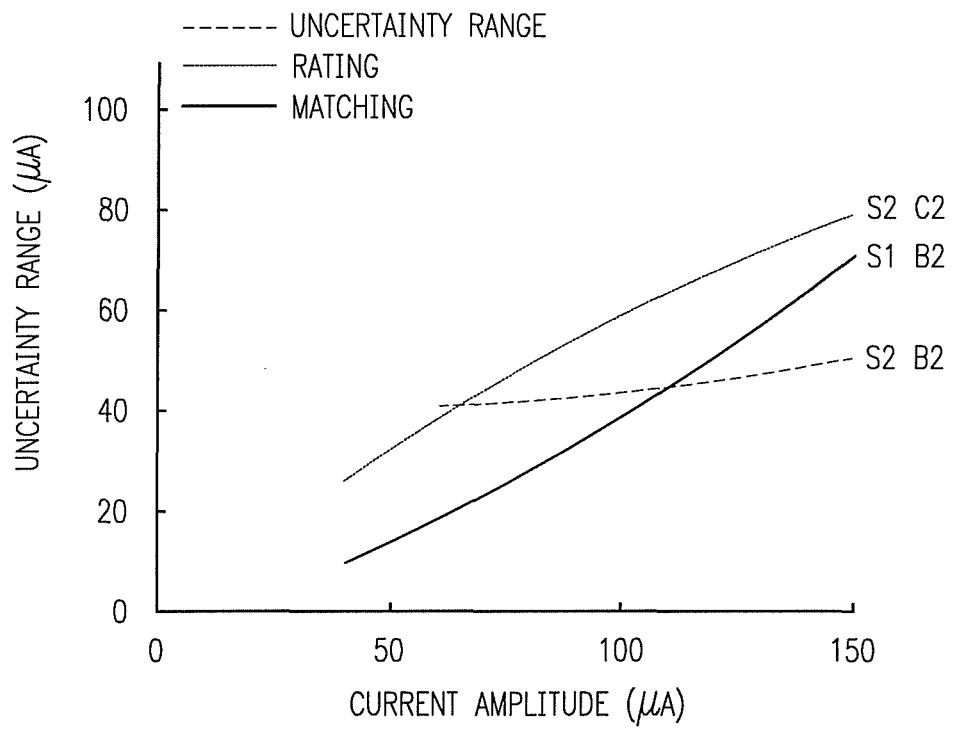
Figure 8A:
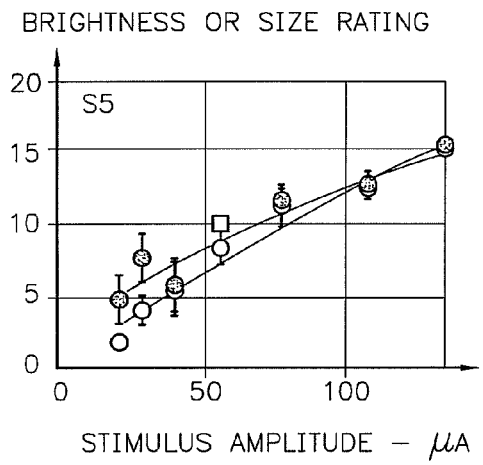
FIGS. 8a-d are graphs showing typical current vs. brightness response.
Figure 8B:
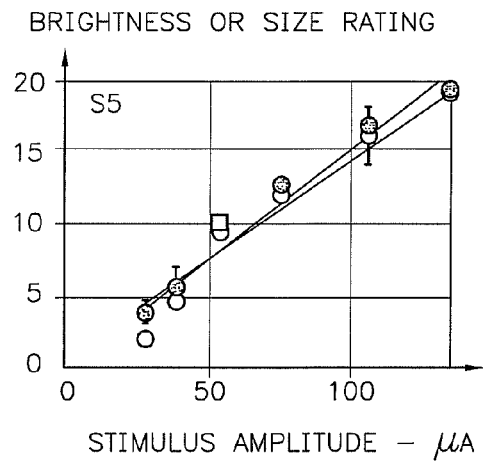
Figure 8C:
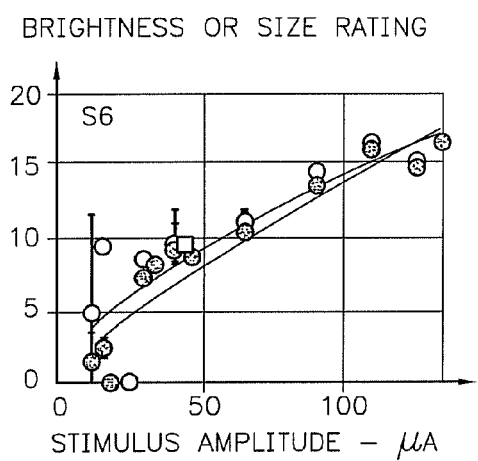
Figure 8D:
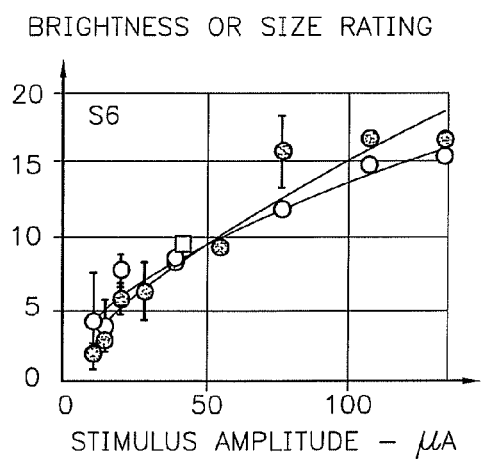

FIG. 5c plots uncertainty range as a function of current amplitude (rating, solid lines) and current amplitude of the reference electrode (matching, dashed lines) for both subjects. Only those electrodes for which both type of measurement was taken are included. Note that the brightness rating task used single pulses, whereas the brightness matching task used pulse trains. However data (not shown) comparing brightness matches for individual pulses as compared to pulse trains on the same electrode do not find any difference in measurement variability between the two types of stimulation. It can be seen that for any given electrode subjects were able to make much finer brightness discriminations when using our matching protocol than they were when using our rating protocol. Using the rating protocol, the size of subjects' standard deviations suggest that they would be able to reliably (with 64% accuracy) differentiate between less than four brightness levels, whereas the standard deviations from our matching protocol suggest that subjects might be able to differentiate up to sixteen different brightness levels.

We show here that apparent brightness does increase systematically as a function of current amplitude in subjects implanted with an epiretinal electrode array. Although all electrodes showed a monotonic increase in brightness as a function of current, different electrodes (even within a single observer) did vary significantly in how brightness increased with current amplitude. The least sensitive electrode required 66% more current than the most sensitive electrode to create an appearance of equal brightness for S1, and required 50% more current for S2.

One factor determining these differences in slope was the size of the electrode, with larger electrodes showing shallower slopes than large electrodes. It should be noted that this result is the opposite of what one might expect, with large electrodes requiring less current to match the reference electrode than small electrodes. It is possible, given the large electrode sizes used in these implants that the current concentrated in a "ring" around the electrode edges, while smaller electrodes would be expected to have more even current distribution across the electrode surface. Another possibility is that the stimulation of a larger retinal area results in greater perceived brightness, analogous to Ricco's law (for small visual stimuli, thresholds decrease as a function of the area subtended by the stimulus).

Given that the function relating current to brightness varies across electrodes, it is necessary to develop some mapping that will permit brightness to be equated across an entire array. As the numbers of electrodes in an array increase, it will be unfeasible to measure full brightness rating and/or brightness matching functions for each individual electrode. Here, we find that that brightness as a function of current amplitude can be described using a power function, with a single scaling factor as a free parameter (see FIG. 2). Equivalently, it is possible to describe relative brightness across electrodes using a linear scaling with a single free parameter (the slope of the brightness matching function of FIG. 4). These results, if they prove to be the case more generally, suggest that it should be possible to normalize brightness across an entire array of electrodes by measuring a single parameter for each electrode. A single brightness matching measurement, if made at a relatively high amplitude, would be sufficient to describe relative sensitivity across electrodes, and thereby provide a simple method of creating the appearance of equally bright phosphenes across an entire array across a wide range of brightness levels.

FIGS. 8a-d show typical perceptual responses collected from four patients. The perceptual responses differ in both the amplitude of the response curve and the shape of the response curve. All four patient perceptual responses, however, can be fitted by the function $B=aI^b$ where B is brightness, I is current amplitude, and a and b are parameters to be estimated from fitting the empirical data. Three data points will adequately define the function. Numerous statistical tools are available for automatically fitting the function to the three data points.

In this example the x axis represent the amplitude of stimulation using a single pulse. The y axis represents the patient's subjective rating of brightness where a stimulus rated as "10" is twice as bright as a stimulus rated as "5".

Figure 9:
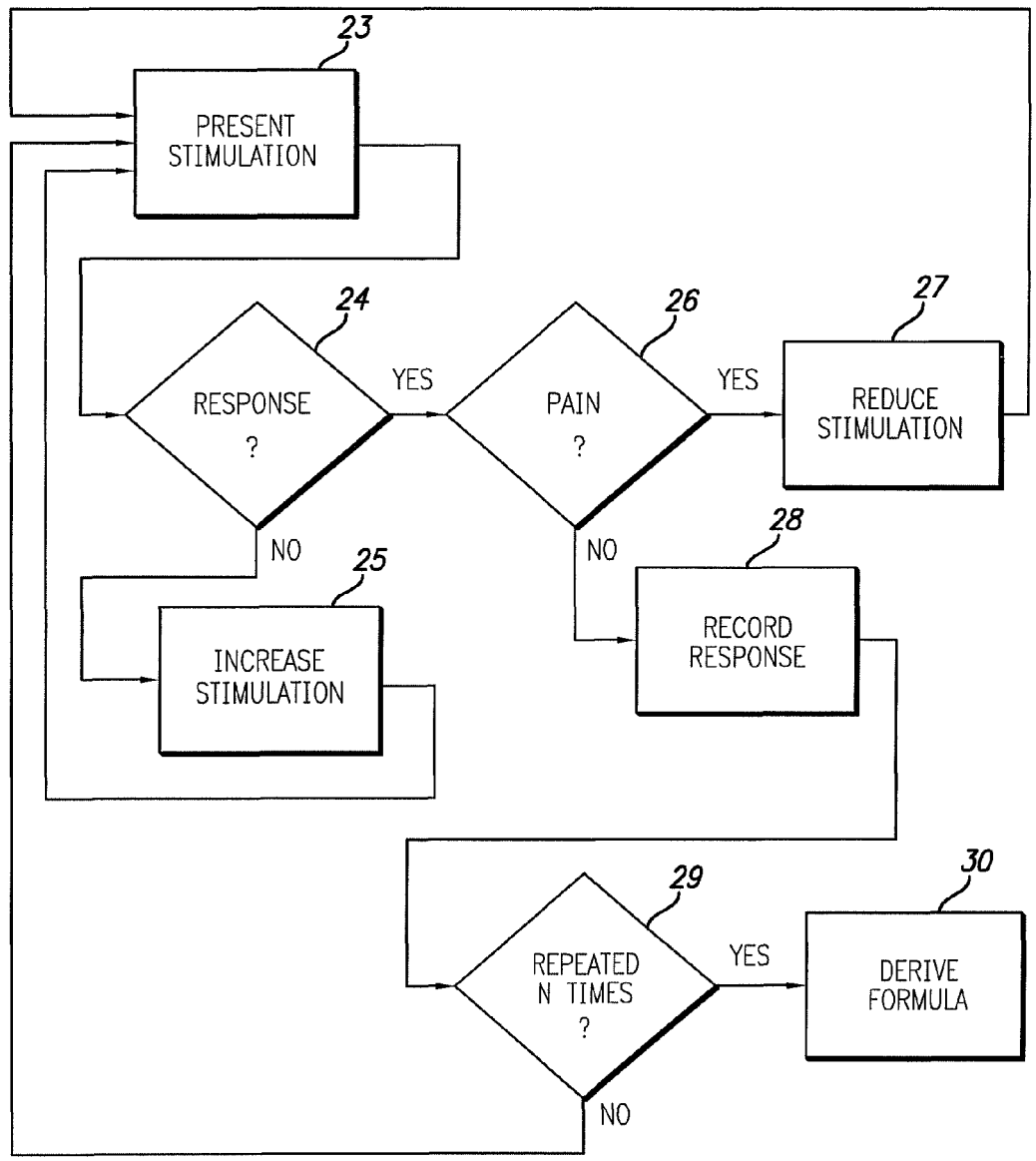
FIG. 9 is a flowchart show the brightness mapping method.

FIG. 9 shows a flow chart of the fitting procedure. In this case, we are using patient's ratings of subjective brightness but a measure of neural actively such a neural recording or pupil response (described below) could be used in an analogous fashion. First the fitting system must determine the perceptual brightness response to current relationship. This is accomplished by stimulating and measuring the subject reported brightness response rating at three points. It should be noted that the response is near linear in most cases. Hence, two points can be used to approximate the response, but three points will yield a more accurate fit. First, a stimulus is presented 23. If there is no response 24, the stimulus is increase 25 and stimulation is presented again 23. If there is a response to stimulus 24 and the response is pain 26, the stimulation is reduced 27 and stimulation is presented again 23. If there is a non-painful response it is recorded 28 in in non-volatile memory of the prosthesis device. Recording the response may include subjective response, neural recording or other physiological response. This process is repeated to get the required number of recorded responses, usually 3. If there are three recorded responses 29, an equation or formula is derived to describe the relationship between current and brightness relationship 30. The formula may be saved as an actual equation to be applied to the input value, or as a table of input and output values. It should also be noted that there must be a maximum charge limit sent in a visual prosthesis for safety reasons. Hence, the current variations must be limited by the preprogrammed maximum change. In the preferred embodiment, current is mapped to brightness. It should be noted that other a factors which may affect brightness, such as voltage, pulse width or frequency, may be mapped by the same method.

After the formula is established, input is received by the camera; the formula is applied to input data; and an output value is used to stimulate neural tissue.

Figure 10:
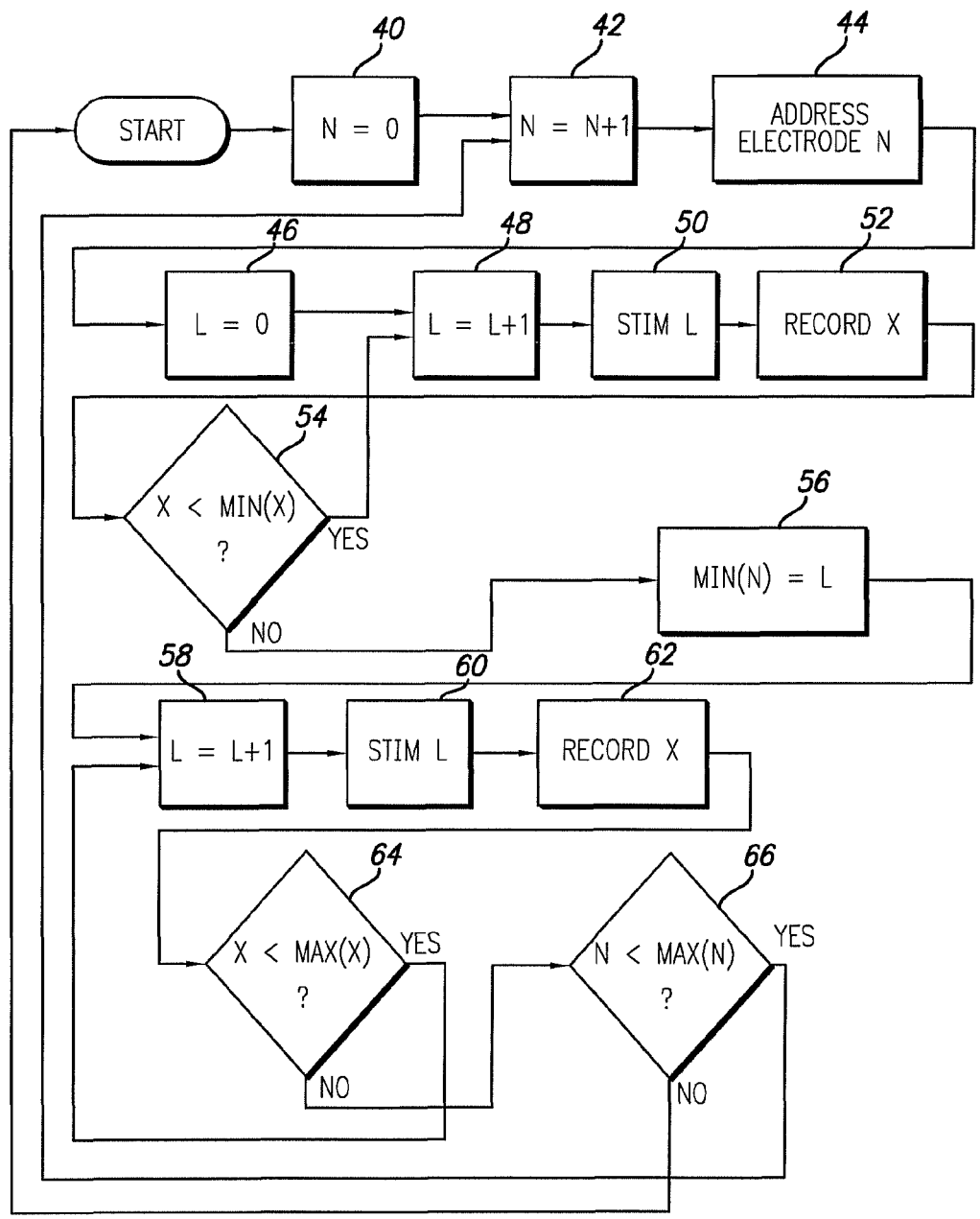
FIG. 10 is a flow chart showing an alternate process of auto fitting an electrode array.

FIG. 10 is a flow chart of an automatic fitting sequence which may be employed to gain the three points needed for the method described in FIG. 9, or may be used as an alternative fitting procedure. In the flow chart, the value N is the selected electrode, X is the neural activity recorded, and L is the level of stimulation (current amplitude. First N is set to 0 40 and then incremented 42. The first electrode, electrode N, is addressed 44. The stimulation level is set to zero 46, and then incremented 48. The neural tissue is stimulated at the minimum level 50. The stimulation is immediately followed by a recording of activity in the neural tissue 52. Alternatively, recording can be done simultaneously by an adjacent electrode. If recording is done simultaneously, one must distinguish between neural activity and electrical charge from the stimulating electrode. The neural response follows stimulation (see FIG. 12). Simultaneous stimulation and recording requires that the recording phase be longer than the stimulation phase. If so, the stimulation and neural response can be separated digitally. If the recorded neural activity is less than a predetermined level 54, the stimulation level is increased and steps 48-54 are repeated.

In most cases, the preset minimum level is any measurable neural activity. However, perception by the patient is the determining factor. If neural activity is detected and the patient reports no perception, the minimum level must be set higher. Once minimum neural activity is recorded, the stimulation level is saved in memory 56. The level is then further increased 58 and stimulation is repeated 60. Again stimulation is immediately followed by recording neural activity 62. If a predetermined maximum level has not been reached, steps 58-64 are repeated until the predetermined maximum stimulation level is obtained. Once the predetermined maximum stimulation level is obtained, steps 42-64 are repeated for the next electrode. The process is continued until a minimum and maximum stimulation level is determined for each electrode 66.

To obtain the subjective brightness or neural response for the necessary three points, one first finds the stimulus amplitude (the intensity of the stimulus can also be varied along other dimensions) which is barely detectable by the patient or provokes a minimally detectable neural response. One then presents the stimulus at that value (e.g. the amplitude value V=42) repeatedly until one has an accurate measurement of the subjective brightness or neural response at that stimulus intensity. One then finds the stimulus amplitude that is just under the safety limit or pain threshold, and measures the apparent brightness or neural response at that stimulus intensity. Finally one finds apparent brightness or neural response for a stimulus whose amplitude is halfway (or intermediate) between those two points. If additional data points are desired, equal distant points such as 25% and 75% should be used.

The range of intensities used for stimulation during operation of the device will fall within the range that is measured during the fitting procedure. Very low or high intensity values may not be used in normal function.

The maximum stimulation level borders on discomfort for the patient. Because the automatic fitting process is automated, high levels of stimulation are only applied for a few microseconds. This significantly decreases the level of discomfort for the patient compared with stimulating long enough to elicit a response from the patient.

The fitting process is described above as an incremental process. The fitting process may be expedited by more efficient patterns. For example changes may be made in large steps if it the detected response is significantly below the desired response, followed by increasingly small steps as the desired response draws near. The system can jump above and below the desired response dividing the change by half with each step.

Often, neural response in a retina is based, in part, on geographical closeness. That is, neurons closer to the fovea require less stimulation than neurons farther from the fovea. Hence once a stimulation is level is set for an electrode, one can presume that the level will be similar for an adjacent electrode. The fitting process may be expedited by starting at a level near the level set for a previously fit adjacent electrode.

Automating the fitting process has many advantages. It greatly expedites the process reducing the efforts of the patient and clinician. Further, the automated process based on measured neural responses is objective. Patient perceptual responses are subjective and may change over time due to fatigue. In some cases, a patent may not be able to provide the required responses due to age, disposition, and/or limited metal ability.

Figure 11:
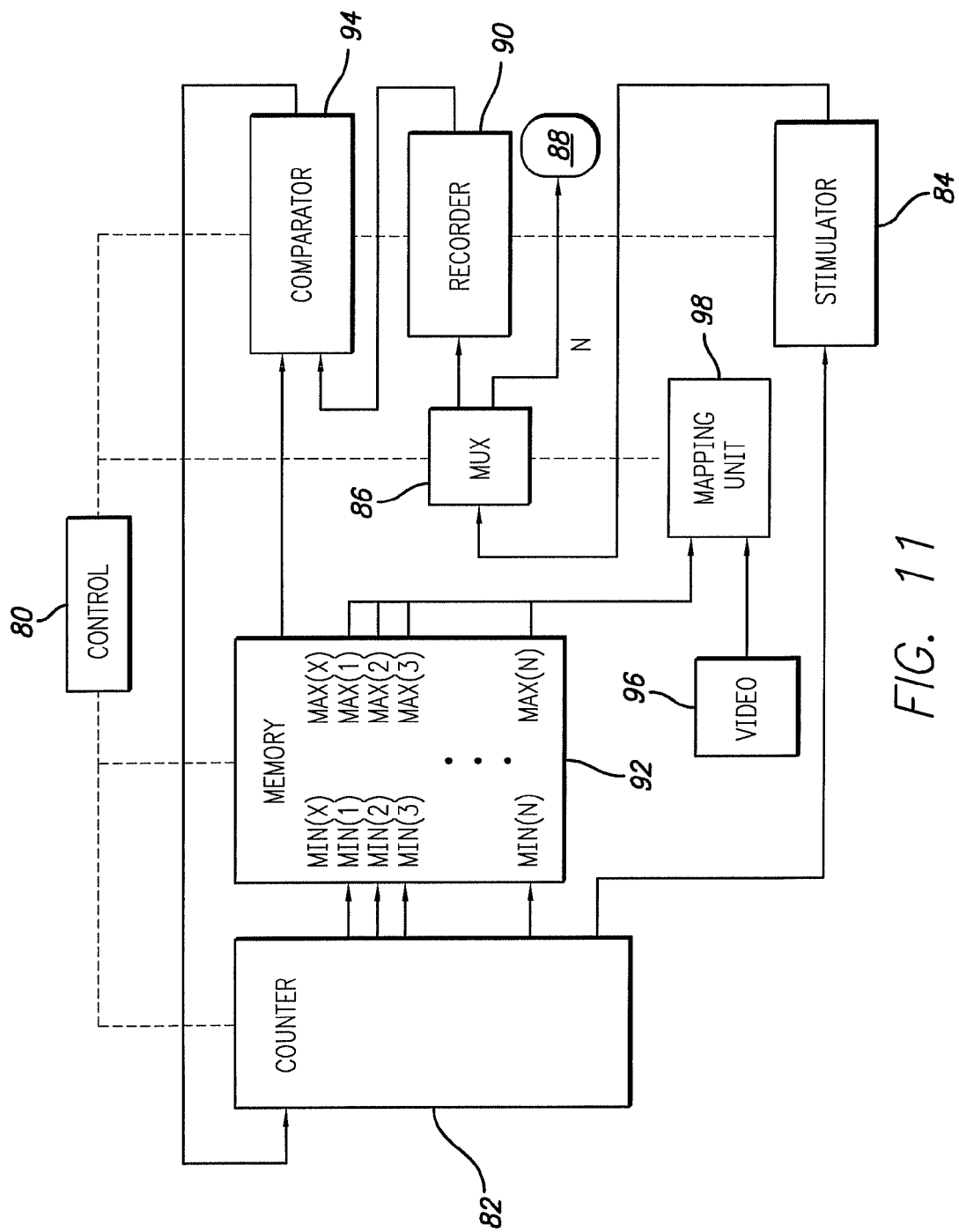
FIG. 11 depicts a block diagram of the retinal prosthesis electronic control unit.

FIG. 11 depicts a block diagram of the control unit. The block diagram is a functional diagram. Many of the functional units would be implemented in a microprocessor. A control unit 80 sets and increments a counter 82 to control the stimulation level of the stimulator 84. The stimulation signal is multiplexed in MUX 86 to address individual electrodes 88. After each stimulation, the addressed electrode returns a neural activity signal to a recorder 90. The signal is compared to the stored minimum or maximum level (stored in a memory 92) in a comparator 94. After programming, a signal from a video source 96, or other neural stimulation source, is adjusted in a mapping unit 98, in accordance with the minimum and maximum levels stored in the memory 92. The adjusted signal is sent to the stimulator 84, which in synchronization with MUX 86 applies the signal to the electrodes 88. The electronics for the control unit could be external or within the implanted prosthesis.

Figure 12:
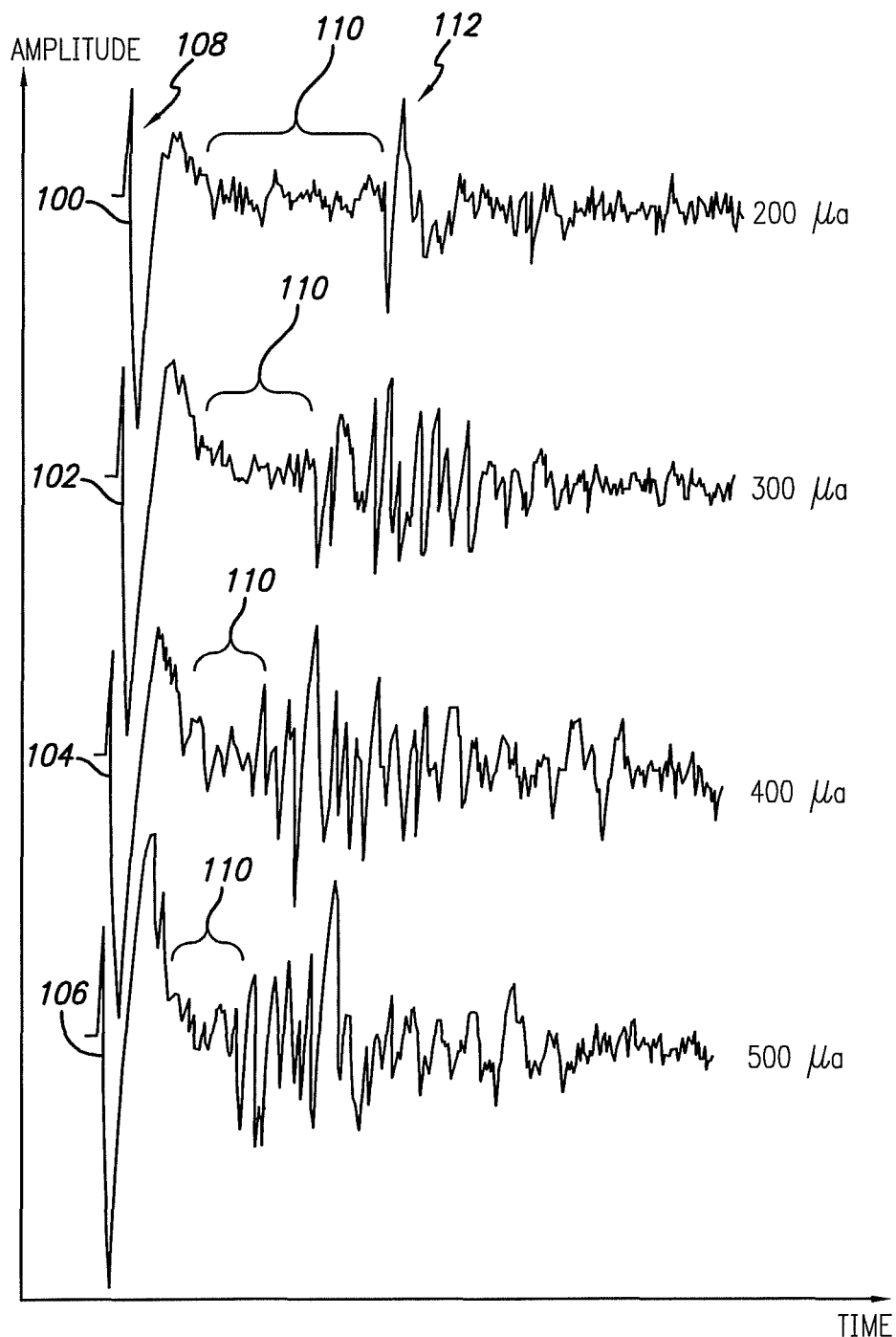
FIG. 12 is a graph depicting a typical neural response to electrical input.

FIG. 12 is a graphical representation of the neural response to electrical stimulus. This figure is derived from actual recordings of a frog retina. Response in a human retina will be similar and can be measured by a retinal electrode, implanted cortical electrode, or external cortical electrode commonly known as a visual evoked response or VEP. The vertical axis is current while the horizontal axis is time. Four curves 100-106 show the response at varying input current levels. An input pulse 108, is followed by a brief delay 110, and a neural response 112. Hence, it is important to properly time the detecting function. Either the stimulating electrode must be switched to a detecting electrode during the brief delay or detecting must occur on another electrode and continue long enough to record the neural response. It should also be noted that the delay period 110 becomes shorter with increased stimulation current. Hence, the system must switch faster from stimulation mode to detecting mode with increased current. The change in delay time may also be used as an additional indication of neural response. That is, the minimum and maximum may be determined by matching predetermined delay times rather than predetermined output levels. As stimulation increases, it becomes more useful to employ an alternate recording means as described in the following alternate embodiments.

In a first alternate embodiment, the recording electrode may be cortical electrode mounted on or near the visual cortex. Temporary external electrodes placed on the scalp proximate to the visual cortex may record neural activity in the visual cortex. This allows the system to account for any variations in neural processing between the retina and the visual cortex. It, however, requires electrodes either implanted in the visual cortex or placed temporarily near the visual cortex. This alternate embodiment may be combined with the preferred embodiment by first using cortical electrodes to perform an initial fitting of the prosthesis in a clinic. Thereafter, retinal recording may be used to readjust the prosthesis for any changes over time.

Figure 13:
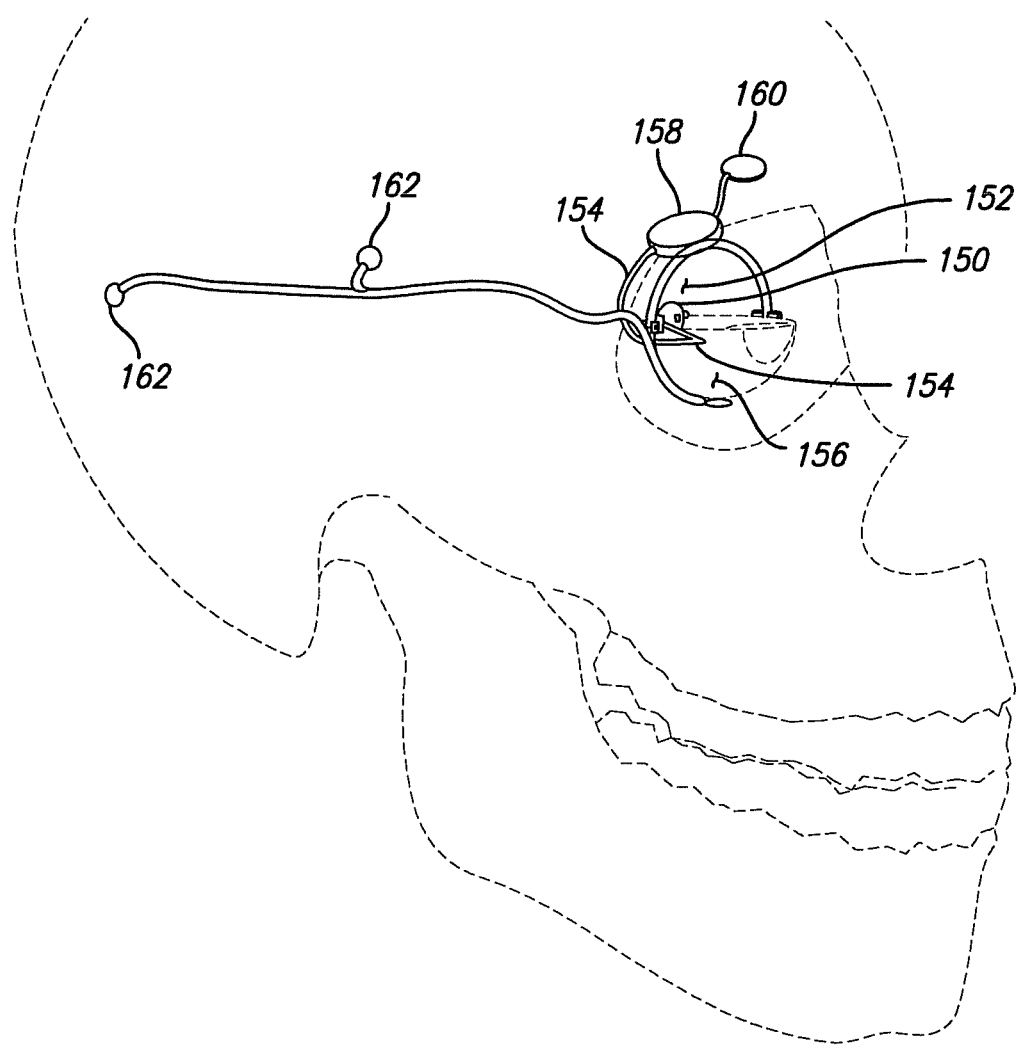
FIG. 13 depicts an alternate fitting process using cortical recording.

FIG. 13 shows the first alternate retinal prosthesis. A stimulating electrode array 150 is placed against the outer surface of a retina 152 (epiretinally). A cable 154 pierces a sclera 156 and attaches to an electronic control unit 158. A return electrode 160 may be placed distant from the retina 152. The stimulating electrode array 150 is a plurality of tiny electrodes. One or more recording electrodes 162 are placed in near the visual cortex. The recording electrodes may be temporary external electrodes, implanted electrodes under the scalp, or electrode implanted within the visual cortex.

In a second alternate embodiment, the recording electrode may be either implanted in the iris, or placed externally near the iris. The iris contracts when increasing light levels enter the eye. Electrical stimulation of the retina also causes the iris to contract, because the body perceives an increase in light entering the eye. Conversely, the iris expands in response to a decrease in electrical stimulation. While the response of the iris is relatively slow, the neurological signals initiating a change in the iris respond quicidy. Measuring these signals may provide alternate feed back as to the body's response to the electrical stimulus. Alternatively, an optical device aimed at the eye may detect the diameter of the iris.

Figure 14:
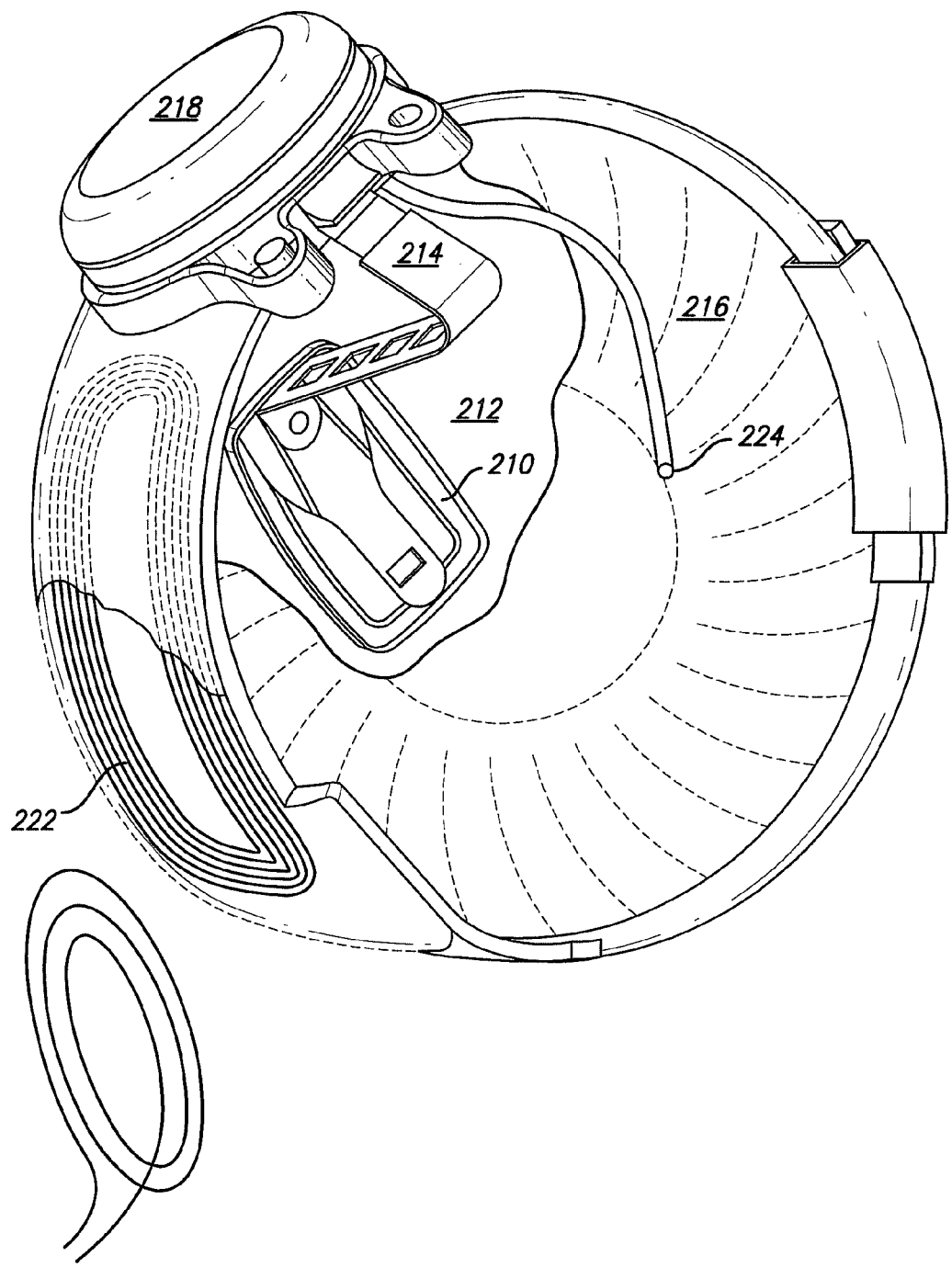
FIG. 14 depicts an alternate fitting process using iris recording.

FIG. 14 shows the second alternate retinal prosthesis. A stimulating electrode array 210 is placed against the outer surface of a retina 212 (epiretinally). A cable 214 pierces a sclera 216 and attaches to an electronic control unit 218, which is connected to secondary coil 222. A return electrode may be formed from the casing for the electronics control unit 218 or may be separate but should be placed distant from the retina 212. The stimulating electrode array 210 is a plurality of tiny electrodes. A recording electrode 224 is place in the periphery of the iris sensing electrical stimulus to the iris.

In a third alternate device, electroluminescent pigments may be applied to the retina. Electroluminescent pigments cause an individual cell to glow when it fires an action potential. A camera of the type used for retinal photos may detect neural response by detecting the electroluminescent glow of the applied pigment.

According to a first aspect, the invention is a method of fitting a visual prosthesis, comprising:
applying a plurality of stimuli via a first selected electrode to visual neural tissue; measuring brightness responses to said stimuli; deriving a first formula based upon said brightness responses; applying a stimuli via a second selected electrode measuring a brightness response to said stimuli; deriving a second formula based on said first formula and said brightness response to said second selected electrode; and generating said stimuli by applying said first formula and said second formula to visual input.

According to a second aspect, the invention is the method according to aspect 1, wherein said stimuli vary according to applied current.

According to a third aspect, the invention is the method according to aspect 1, wherein said stimuli vary according to applied voltage.

According to a forth aspect, the invention is the method according to aspect 1, wherein said stimuli vary according to applied frequency.

According to the fifth aspect, the invention is the method according to aspect 1, wherein said stimuli vary according to applied pulse width.

According to the sixth aspect, the method according to aspect 1, wherein said brightness responses are perceptions of brightness reported by a user.

According to the seventh aspect, the invention is the method according to aspect 1, wherein said responses are neural responses recorded from the visual neural tissue of the user.

According to the eighth aspect, the invention is the method according to aspect 1, wherein said responses are recorded physiological changes in the iris of a user.

According to the ninth aspect, the invention is the method according to aspect 1, wherein said responses are recorded neural activity of the user.

According to the tenth aspect, the invention is the method according to aspect 1, further comprising creating a table based on said formula.

According to the eleventh aspect, the invention is the method according to aspect 10, wherein said step of generating stimuli by applying said formula comprises applying values from said table.

According to the twelfth aspect, the invention is the method according to aspect 1, wherein said formula defines brightness as slope times current to the power of shape where slope and shape are derived terms.

According to the thirteenth aspect, the invention is the method according to aspect 1, wherein said formula defines brightness as slope time current plus threshold where slope and threshold are derived terms.

Accordingly, what has been shown are fitting techniques and an improved method of matching brightness to stimulation parameters. While these techniques have been described by means of specific embodiments and applications thereof, it is understood that numerous modifications and variations could be made thereto by those skilled in the art without departing from the spirit and scope of the disclosure. It is therefore to be understood that within the scope of the claims, the disclosure may be practiced otherwise than as specifically described herein.

We claim:

1. A method of fitting a visual prosthesis, comprising:
   applying a plurality of stimuli via a first selected electrode to visual neural tissue;
   measuring brightness responses to said stimuli;
   deriving a formula based upon said brightness responses;
   applying a stimuli via a second selected electrode;
   measuring a brightness response to said stimulus applied to said second electrode;
   deriving a constant based on brightness matching measurement of said reference stimulus on said first selected electrode and said stimulus on said second selected electrode; and
   generating further stimuli on said second electrode by applying said formula offset by said constant to visual input.

2. The method according to claim 1, wherein said stimuli vary according to applied current.

3. The method according to claim 1, wherein said stimuli vary according to applied voltage.

4. The method according to claim 1, wherein said stimuli vary according to applied frequency.

5. The method according to claim 1, wherein said stimuli vary according to applied pulse width.

6. The method according to claim 1, wherein said brightness responses are perceptions of brightness reported by a user.

7. The method according to claim 1, wherein said responses are neural responses recorded from the visual neural tissue of the user.

8. The method according to claim 1, wherein said responses are recorded physiological changes in the iris of a user.

9. The method according to claim 1, wherein said responses are recorded neural activity of the user.

10. The method according to claim 1, further comprising creating a table based on said formula.

11. The method according to claim 10, wherein said step of generating stimuli by applying said formula comprises applying values from said table.

12. The method according to claim 1, wherein said formula defines brightness as slope times current to the power of shape where slope and shape are derived terms.

* * * * *